United States Patent
Kang et al.

(10) Patent No.: US 11,707,434 B2
(45) Date of Patent: Jul. 25, 2023

(54) METHOD FOR PREPARING ORGANIC SOLVENT-FREE LYOPHILIZED CYCLOPHOSPHAMIDE

(71) Applicant: KOREA UNITED PHARM. INC., Sejong-si (KR)

(72) Inventors: Won Ho Kang, Seoul (KR); Won Tae Jung, Seoul (KR); Jung Hoon Kang, Gyeonggi-do (KR); Youn Woong Choi, Gyeonggi-do (KR)

(73) Assignee: KOREA UNITED PHARM. INC., Sejong-si (KR)

( * ) Notice: Subject to any disclaimer, the term of this patent is extended or adjusted under 35 U.S.C. 154(b) by 198 days.

(21) Appl. No.: 17/047,174

(22) PCT Filed: Apr. 11, 2019

(86) PCT No.: PCT/KR2019/004355
§ 371 (c)(1),
(2) Date: Oct. 13, 2020

(87) PCT Pub. No.: WO2019/199076
PCT Pub. Date: Oct. 17, 2019

(65) Prior Publication Data
US 2021/0177764 A1    Jun. 17, 2021

(30) Foreign Application Priority Data

Apr. 13, 2018 (KR) .................. 10-2018-0043391

(51) Int. Cl.
*A61K 9/19* (2006.01)
*A61K 31/675* (2006.01)
*A61K 47/26* (2006.01)

(52) U.S. Cl.
CPC .............. *A61K 9/19* (2013.01); *A61K 31/675* (2013.01); *A61K 47/26* (2013.01)

(58) Field of Classification Search
None
See application file for complete search history.

(56) References Cited

U.S. PATENT DOCUMENTS

| 4,659,699 | A |   | 4/1987 | Francis |
| 4,879,286 | A |   | 11/1989 | Alam et al. |
| 5,036,060 | A | * | 7/1991 | Alam ............... A61K 31/675 |
|           |   |   |        | 514/110 |
| 5,413,995 | A |   | 5/1995 | Alexander et al. |

FOREIGN PATENT DOCUMENTS

| KR | 10-2018-0041814 A | 4/2018 |
| WO | 2014068585 A1 | 5/2014 |

OTHER PUBLICATIONS

Hiwale et al. (Variable Affecting Reconstitution Time of Dry Powder for Injection, Jul. 2, 2008). (Year: 2008).*
Korean Intellectual Property Office, International Search Report and Written Opinion for PCT/KR2019/004355 dated Jul. 23, 2019, 12 pages.

* cited by examiner

*Primary Examiner* — Melissa S Mercier
(74) *Attorney, Agent, or Firm* — Edwin S. Flores; Daniel J. Chalker; Chalker Flores, LLP

(57) ABSTRACT

The present invention relates to a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, comprising a step of dissolving D-mannitol or lactose, as a lyoprotectant, and cyclophosphamide in a water solvent in a selected reaction vessel; and a lyophilized cyclophosphamide composition for injection prepared thereof.

18 Claims, 5 Drawing Sheets

METHOD FOR PREPARING ORGANIC SOLVENT-FREE LYOPHILIZED CYCLOPHOSPHAMIDE

CROSS-REFERENCE TO RELATED APPLICATIONS

This application is the National Stage of International Application No. PCT/KR2019/004355, filed on Apr. 11, 2019 claiming the priority of KR 10-2018-0043391, filed on Apr. 13, 2018, the content of each of which is incorporated by reference herein.

TECHNICAL FIELD OF THE INVENTION

The present invention relates to a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, which includes a step of dissolving D-mannitol or lactose, as a lyoprotectant, and cyclophosphamide in a water solvent in a selected reaction vessel; and a lyophilized cyclophosphamide composition for injection prepared therefrom.

BACKGROUND OF THE INVENTION

Cyclophosphamide is a synthetic anticancer drug represented by the formula below, which is chemically related to nitrogen mustard:

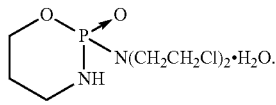

Cyclophosphamide is an example of cyclic phosphoric acid ester amides disclosed in U.S. Pat. No. 3,018,302 registered on Jan. 23, 1962. The chemical name of cyclophosphamide is 2-[bis(2-chloroethyl)amino]tetrahydro-2H-1,3,2-oxazaphosphorin-2-oxide, and it exists in a monohydrate or anhydrous form. Although cyclophosphamide is usually used in the form of a monohydrate, it may lose water molecules and become anhydrous in a dry condition having a relative humidity of 20% or below or during a preparation process.

Cyclophosphamide was initially distributed in the form of a monohydrate, but it was also provided in a parenteral dose of a pre-mixture consisting of a dry powdered mixture containing drugs and sodium chloride through sterilization and packaging. In addition, cyclophosphamide could be administered not only parenterally but also orally after dissolving the pre-mixture in water prior to administration. However, since the shelf-life of an aqueous solution thereof was only a few hours after its preparation, it was necessary to immediately administer the same upon preparation. Meanwhile, with respect to the formulation type of the pre-mixture in a dry powdered state, the pre-mixture composition could be hyalinized or become sticky during a preparation process and/or storage period, and additionally, the pre-mixture composition sometimes had poor properties (e.g., a decrease in solubility, effects, etc.). Such deterioration occurred when the storage period became long or the storage temperature was higher than the recommended upper limit.

Recently, cyclophosphamide has been distributed in the form of a lyophilizate. Although lyophilization has been used for injections of drugs that are insoluble in an aqueous solution, it was not until around 1982 that lyophilization was applied to cyclophosphamide. Since then, studies have been conducted on lyophilized compositions containing cyclophosphamide as an active ingredient and on preparation methods thereof using various additives, but most methods were carried out using an organic solvent, such as butanol, etc. When even trace amounts of these organic solvents remain in the body, they may cause irritation of the body or exhibit harmful side effects. Therefore, there is an inconvenience in that these organic solvents must be removed below the acceptable residual standard.

Technical Problem

The present inventors have made extensive efforts to discover a method for preparing a lyophilized cyclophosphamide composition without using an organic solvent. As a result, they have confirmed that a lyophilized composition with improved stability and solubility can be prepared by adjusting the temperature for dissolving cyclophosphamide, which is an active ingredient of the lyophilized composition, while using an aqueous solution that does not contain an organic solvent, thereby completing the present invention.

Technical Solution

An object of the present invention is to provide a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, which includes a first step of dissolving D-mannitol or lactose, as a lyoprotectant, and cyclophosphamide in a water solvent in a reaction vessel at 40° C. to 70° C.; a second step of filling the solution obtained in the previous step into a vial prepared by sterilization; and a third step of lyophilizing the cyclophosphamide solution filled into the vial.

Another object of the present invention is to provide a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, which includes a first step of dissolving 0.01 g to 0.1 g of cyclophosphamide per 1 mL of a water solvent based on weight of the anhydrous cyclophosphamide; and 5 to 250 parts by weight of D-mannitol or lactose based on 100 parts by weight of the anhydrous cyclophosphamide in the water for pharmaceutical use in a reaction vessel at 40° C. to 70° C.; a second step of sterilizing the solution obtained in the previous step by filtration with a membrane having a size of 0.2 μm or less and dispensing the solution into a container for injection; a third step of lyophilizing the solution dispensed into the container to form a lyophilized cake; and a fourth step of sealing.

Still another object of the present invention is to provide a lyophilized composition for injection, comprising 6 to 8 parts by weight of water and 5 to 250 parts by weight of D-mannitol or lactose based on 100 parts by weight of anhydrous cyclophosphamide, wherein 99% or more of the lyophilized composition for injection is reconstituted within 15 seconds when water for pharmaceutical use is injected thereinto at a ratio of 50 mL per 1 g of the anhydrous cyclophosphamide.

Still another object of the present invention is to provide a method for preparing a cyclophosphamide injection, which includes a first step of dissolving cyclophosphamide and D-mannitol or lactose in a water solvent in a reaction vessel at 40° C. to 70° C.; a second step of lyophilizing the solution obtained in the previous step to prepare a lyophilized cyclophosphamide composition; and a third step of adding 50 mL of water for pharmaceutical use to the lyophilized cyclophosphamide composition, which is obtained in the previous step, per 1 g of anhydrous cyclophosphamide.

SUMMARY OF THE INVENTION

The preparation method of the present invention can completely dissolve insoluble raw materials without using an organic solvent by adding a certain amount of a lyoprotectant (e.g., D-mannitol) and dissolving the same by increasing the temperature to a certain range in the preparation of a solution of cyclophosphamide (i.e., an insoluble material) prior to lyophilization. In addition, the preparation method of the present invention not only provides the composition with improved stability and solubility by lyophilizing the same, but also reduces risks that may occur due to residual organic solvents when organic solvents are used. Further, the preparation method of the present invention has an effect of reducing insoluble particles produced when organic solvents are used. Moreover, when the cyclophosphamide solution is prepared in a lyophilized formulation, its solubility is enhanced compared to those of conventional powdered products. Therefore, the time of completely dissolving active ingredients can be significantly shortened to within a few seconds to less than 20 seconds when water for pharmaceutical use is added thereto, and thereby the preparation method of the present invention provides convenience when it is actually used in the field.

BEST MODE FOR CARRYING OUT THE INVENTION

Figure 1:
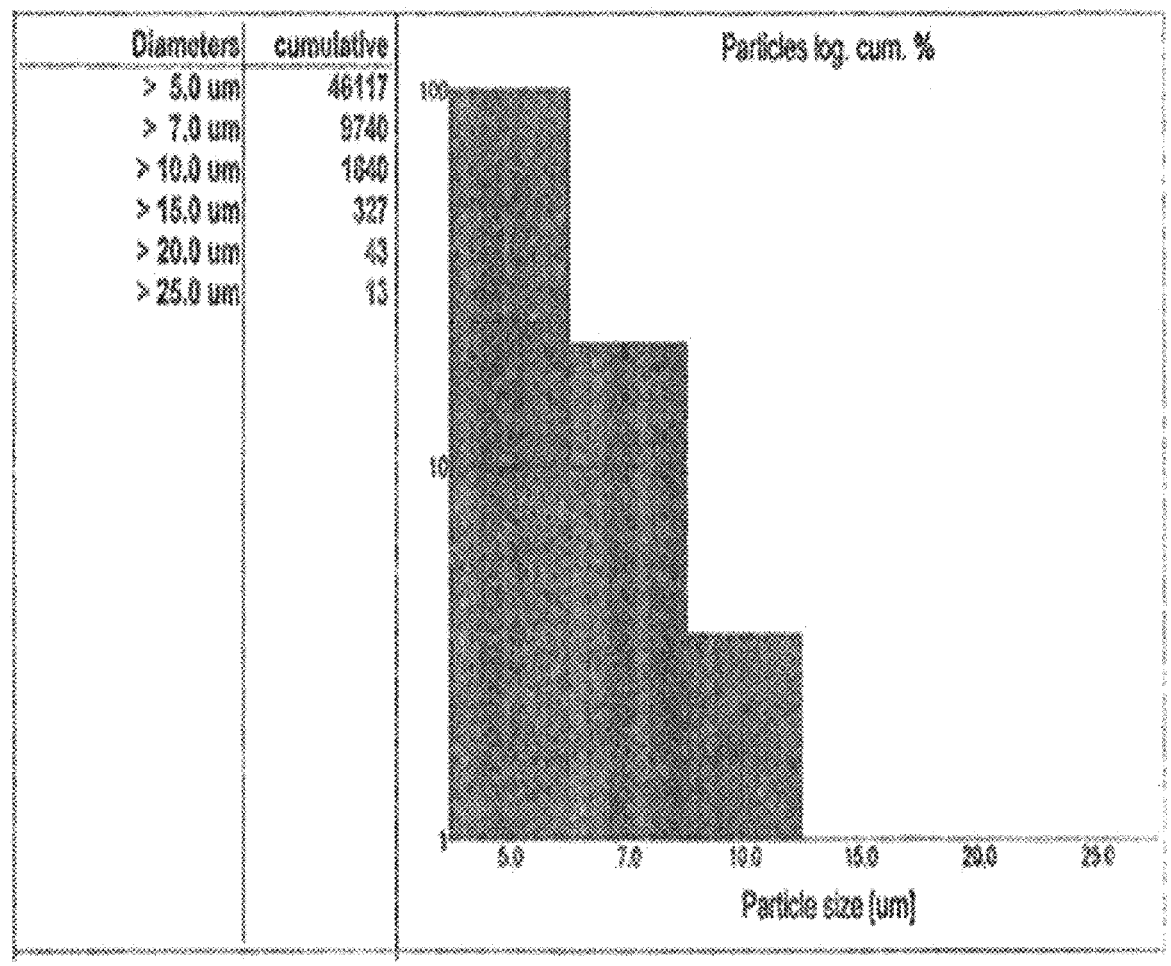
FIG. 1 is a graph illustrating the results of insoluble particle counts measured for a lyophilized cyclophosphamide composition according to the present invention.

To achieve the above objects, a first aspect of the present invention provides a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, which includes a first step of dissolving D-mannitol or lactose, as a lyoprotectant, and cyclophosphamide in a water solvent in a reaction vessel at 40° C. to 70° C.; a second step of filling the solution obtained in the previous step into a vial prepared by sterilization; and a third step of lyophilizing the cyclophosphamide solution filled into the vial.

A second aspect of the present invention provides a method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, which includes a first step of dissolving 0.01 g to 0.1 g of cyclophosphamide per 1 mL of a water solvent based on weight of the anhydrous cyclophosphamide; and 5 to 250 parts by weight of D-mannitol or lactose based on 100 parts by weight of the anhydrous cyclophosphamide in the water for pharmaceutical use in a reaction vessel at 40° C. to 70° C.; a second step of sterilizing the solution obtained in the previous step by filtration with a membrane having a size of 0.2 µm or less and dispensing the solution into a container for injection; a third step of lyophilizing the solution dispensed into the container to form a lyophilized cake; and a fourth step of sealing.

A third aspect of the present invention provides a lyophilized composition for injection, comprising 6 to 8 parts by weight of water and 5 to 250 parts by weight of D-mannitol or lactose based on 100 parts by weight of anhydrous cyclophosphamide, wherein 99% or more of the lyophilized composition for injection is reconstituted within 15 seconds when water for pharmaceutical use is injected thereinto at a ratio of 50 mL per 1 g of the anhydrous cyclophosphamide.

A fourth aspect of the present invention provides a method for preparing a cyclophosphamide injection, which includes a first step of dissolving cyclophosphamide and D-mannitol or lactose in a water solvent in a reaction vessel at 40° C. to 70° C.; a second step of lyophilizing the solution obtained in the previous step to prepare a lyophilized cyclophosphamide composition; and a third step of adding 50 mL to 500 mL of water for pharmaceutical use to the lyophilized cyclophosphamide composition, which is obtained from the previous step, per 1 g of anhydrous cyclophosphamide.

Hereinbelow, the present invention will be described in more detail.

The present invention relates to a method for preparing a lyophilized cyclophosphamide composition (i.e., an insoluble drug) using a water solvent for resolving the safety problem due to the residual solvent, instead of using an organic solvent (e.g., butanol, etc.), which has conventionally been used for the preparation of a lyophilized composition for injection of insoluble drugs. The method of the present invention is based on the discovery that cyclophosphamide, an insoluble raw material, can be completely dissolved while the content and activity of cyclophosphamide are maintained, by maintaining a solution of cyclophosphamide at a specific temperature range and dissolving a suitable amount of a lyoprotectant along with the cyclophosphamide solution in order to completely dissolve cyclophosphamide in a water solvent. Moreover, it was confirmed that by lyophilization of the same, it is possible to provide a lyophilized cyclophosphamide composition with improved stability and solubility when it is re-dissolved in water for injection, compared to the lyophilized compositions which are prepared using a conventional organic solvent or prepared after dissolution at a temperature outside the specific temperature range. In addition, it was confirmed that since the lyophilized composition of the present invention is prepared without using an organic solvent, it is safe in terms of side effects caused by a residual solvent, and is thus suitable for use as an injection.

In particular, when the lyophilized composition is provided in a sealed form after its preparation in a syringe container with an appropriate volume, it is advantageous in that the lyophilized composition is more rapidly dissolved when water for pharmaceutical use is added thereto, and thus the composition can be conveniently used in the field, compared to the conventional compositions prepared in a powdered form, lyophilized compositions prepared using an organic solvent (e.g., t-butanol, etc.), or lyophilized compositions prepared after—dissolution at a temperature outside the specific temperature range.

Specifically, the present invention is characterized by the discovery that the solubility of the lyophilized composition finally produced can be significantly improved by changing the conditions in a specific process (for example, by using a specific lyoprotectant and dissolving it at a specific temperature condition in the step of preparing the raw material solution before lyophilization) while using the conventional process for preparing a lyophilized composition for injection, for the purpose of discovering optimized conditions for discovering a preparation method that can provide a lyophilized composition (i.e., the final product) with a solubility to be completely dissolved within a short period of time (e.g., within less than 20 seconds) to be convenient for use in the field, considering that the lyophilized composition to be finally produced is intended for use as an injection.

The present invention provides a method for preparing a lyophilized cyclophosphamide composition, which includes a first step of dissolving cyclophosphamide and a lyoprotectant in a water solvent in a reaction vessel at 40° C. to 70° C.; and a second step of lyophilizing the solution obtained in the previous step. The preparation method of the present invention is characterized in that the solubility of the finally prepared lyophilized cyclophosphamide composition is significantly improved by adjusting the temperature at which the reactants are dissolved, such that the finally prepared lyophilized cyclophosphamide composition is completely reconstituted (specifically, 99% or more of the composition is dissolved) within 15 seconds when water for pharmaceutical use is injected thereinto at a ratio of 50 mL per 1 g of anhydrous cyclophosphamide. In particular, the water for pharmaceutical use may be water for injection, drinking water, purified water, sterile purified water, sterile water for injection, bacteriostatic water for injection, distilled water, or normal saline.

In the preparation method of the present invention, the first step is characterized in that cyclophosphamide and a lyoprotectant are dissolved in a water solvent at 40° C. to 70° C. By dissolving at the predetermined temperature, the solubility of the lyophilized composition is improved such that when water for injection is added thereto in the field for the eventual use of the lyophilized composition as an injection, 99% or more of the lyophilized composition is immediately dissolved (e.g., within 15 seconds) while the activity and/or content of cyclophosphamide (i.e., the active ingredient contained in the lyophilized composition) is maintained, and thereby, convenience in use can be provided for the lyophilized composition to be prepared therefrom. Meanwhile, when the dissolution in the first step is performed at a temperature below 40 □, the content of cyclophosphamide (i.e., the active ingredient contained in the final lyophilized composition) may be lowered due to incomplete dissolution of cyclophosphamide, or the re-dissolution rate may decrease when water for injection is injected into the final lyophilized composition, or the time required for complete dissolution (e.g., dissolution of 99% or more) may increase. When the dissolution temperature is higher than 70 □, cyclophosphamide is dissolved rapidly within 1 minute, but the content of cyclophosphamide (i.e., the active ingredient) decreases. Meanwhile, when the dissolution is performed at a high temperature above 70 □, the efficacy of cyclophosphamide as a drug may be reduced due to high-temperature treatment even if its content is maintained, or the re-dissolution rate may decrease when water for injection is injected into the final lyophilized composition, or the time required for complete dissolution (e.g., dissolution of 99% or more) may increase.

The amount of cyclophosphamide used for the preparation method of the present invention may be 0.01 g to 0.1 g per 1 mL of a water solvent when the cyclophosphamide is in an anhydrous form. When the amount of the cyclophosphamide used is below 0.01 g/mL, an unnecessarily large amount of a solvent is used to produce a certain amount of a lyophilized cyclophosphamide composition, which results in an increase of the volume of reactants, thereby decreasing the reaction efficiency. In contrast, when the amount of the cyclophosphamide used exceeds 0.1 g/mL, it may result in incomplete dissolution of cyclophosphamide (i.e., the raw material) in a solution.

The term "lyophilization" refers to a drying method in which a sample in a solution state is frozen and left under reduced pressure as it is, and thereby moisture contained in the sample is removed by sublimation. This method can be used for drying a sample that contains water.

However, when the sample containing water is frozen, water molecules are crystallized during freezing while excluding media such as contaminants or solutes, thereby forming ice crystals consisting of only water molecules. As a result, the media of solutes or contaminants in a material containing water may not be diffused uniformly, thereby causing freeze concentration.

Accordingly, in order to overcome such a problem, the lyophilization may be performed by additionally adding to a solution a lyoprotectant (e.g., D-mannitol or lactose) for preventing physical and/or chemical damage and blocking structural changes. In the conventional methods of preparing lyophilized compositions, dimethylsulfoxide (DMSO), dextran, sucrose, glycerol, mannitol, sorbitol, fructose, trehalose, raffinose, serum albumin, etc. may be combined and used as lyoprotectants according to purposes.

The biosafety of these lyoprotectants has already been confirmed. However, since the mixing conditions according to the purposes are complicated, their preparation method is complex and a large cost may be required for their preparation. In this respect, the present inventors have confirmed that among the lyoprotectants, D-mannitol or lactose is effective in preparing a lyophilized cyclophosphamide composition, and thus D-mannitol or lactose was used as a lyoprotectant in the present invention. Specifically, D-mannitol may be used as a lyoprotectant, but the lyoprotectant to be used is not limited thereto.

In a specific embodiment of the present invention, it was confirmed that when D-mannitol or lactose is used as a lyoprotectant, it is advantageous for cake formation of the lyophilized composition to be finally produced. Additionally, it was confirmed that when the lyophilized composition is dissolved by adding water for pharmaceutical use to the prepared cake above, the dissolution time can be reduced due to its excellent permeability. In contrast, when sorbitol, sucrose, dextrose, etc. is used as a lyoprotectant, cake formation was poor compared to when D-mannitol or lactose was used as a lyoprotectant, which may result in an increase of the dissolution time when used in the field (see Examples 7 and 8, Comparative Examples 1 to 3, and FIGS. 3 to 8).

In particular, the lyoprotectant may be used in an amount of 5 to 250 parts by weight based on 100 parts by weight of anhydrous cyclophosphamide, but the amount of the lyoprotectant to be used is not limited thereto.

Specifically, the cyclophosphamide may be used in a concentration of 0.01 g/mL to 0.1 g/mL based on anhydrous cyclophosphamide, and the lyoprotectant may be used in an amount of 5 to 250 parts by weight based on 100 parts by weight of anhydrous cyclophosphamide, but the amounts of the cyclophosphamide and the lyoprotectant are not limited thereto.

In a specific embodiment of the present invention, when D-mannitol, as a lyoprotectant, was used in an amount of 0.1 g to 2 g per 1 g of anhydrous cyclophosphamide, that is, when D-mannitol was added in an amount of 10 to 200 parts by weight based on 100 parts by weight of anhydrous cyclophosphamide, the final lyophilized composition was completely dissolved within 15 seconds upon injection of water for injection (Samples 15 and 16 in Tables 5 and 6).

In addition, a sterilization step may further be included between the first step and the second step. For example, the sterilization step may be performed by filtering through a membrane with a pore size of 0.2 μm or less. For example, the sterilization through filtration using a membrane is achieved by excluding microorganisms according to size, and it can discharge contaminants having a size larger than that of pores on the surface of the membrane.

The membrane currently used for sterilization is a membrane with a pore size of 0.2 μm, but the pore size of the membrane is not limited thereto, and for the removal of viruses, a nanofiltration membrane with a smaller pore size of 20 nm to 50 nm may be used.

Meanwhile, the third step may be performed by cooling and maintaining the temperature at −40° C. or below while maintaining a vacuum of 200 mTorr to 1,000 mTorr, but the conditions are not limited thereto, and the third step may be performed using a lyophilization method known in the art. Specifically, the third step may be performed by cooling and maintaining the temperature at −40° C. or below; maintaining a vacuum of 200 mTorr to 1,000 mTorr and while maintaining the pressure level at the range above, increasing the temperature in a stepwise manner during which the temperature is periodically maintained for a certain period of time, but the third step is not limited thereto. For example, in a specific embodiment of the present invention, the lyophilization was performed in such a manner that the temperature was cooled to −40° C. and maintained for 300 minutes; and the pressure was reduced to 250 mTorr, and while the temperature sequentially increased to −15° C. and then 0° C. in a stepwise manner, the temperature was maintained for 1,620 minutes and 2,760 minutes, respectively.

In particular, the third step may be performed in a container for injection. As described above, since cyclophosphamide (i.e., the lyophilized composition of the present invention) is relatively unstable in a solution state, it is preferable to immediately use cyclophosphamide upon preparation of the same in the solution state by adding an injection. Therefore, in order to provide cyclophosphamide for injection, it is preferable to provide cyclophosphamide in a syringe container by dispensing according to an amount per use. However, once a composition is lyophilized, it is difficult to precisely weigh and dispense the composition for an injection amount per use. Therefore, the composition is lyophilized by directly dispensing an adequate amount thereof to a container for injection in a solution state so that the lyophilized composition containing a certain amount of cyclophosphamide can be easily prepared.

Specifically, a sealing step may further be included after the third step. The sealing step may be performed using a conventional method known in the art, and it may be performed by replacing with nitrogen, but the sealing step is not limited thereto.

For example, the preparation method of the present invention can provide a lyophilized composition in the form of a cake having a porosity of 40% to 90%.

In addition, the lyophilized cyclophosphamide composition of the present invention with improved safety and solubility, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, can be prepared by a method, which includes a first step of dissolving 0.01 g to 0.1 g of cyclophosphamide per 1 mL of a solvent based on weight of the anhydrous cyclophosphamide and 5 to 250 parts by weight of lyoprotectant based on 100 parts by weight of the anhydrous cyclophosphamide in the water for pharmaceutical use in a reaction vessel at 40° C. to 70° C.; a second step of sterilizing the solution obtained in the previous step by filtration with a membrane having a size of 0.2 μm or less and dispensing the solution into a container for injection; a third step of lyophilizing the solution dispensed into the container to form a lyophilized cake; and a fourth step of sealing.

Further, the present invention can provide a lyophilized composition for injection, which contains 6 to 8 parts by weight of water and 5 to 250 parts by weight of a lyoprotectant based on 100 parts by weight of anhydrous cyclophosphamide. The lyophilized composition for injection is characterized in that 99% or more of the lyophilized composition for injection can be reconstituted within 15 seconds when water for pharmaceutical use is injected thereinto at a ratio of 50 mL per 1 g of the anhydrous cyclophosphamide.

The lyophilized composition of the present invention may be prepared by the method according to the first aspect of the present invention. Specifically, the lyophilized composition of the present invention may be prepared by the method according to the second aspect of the present invention, but the preparation method is not limited thereto.

Figure 2:
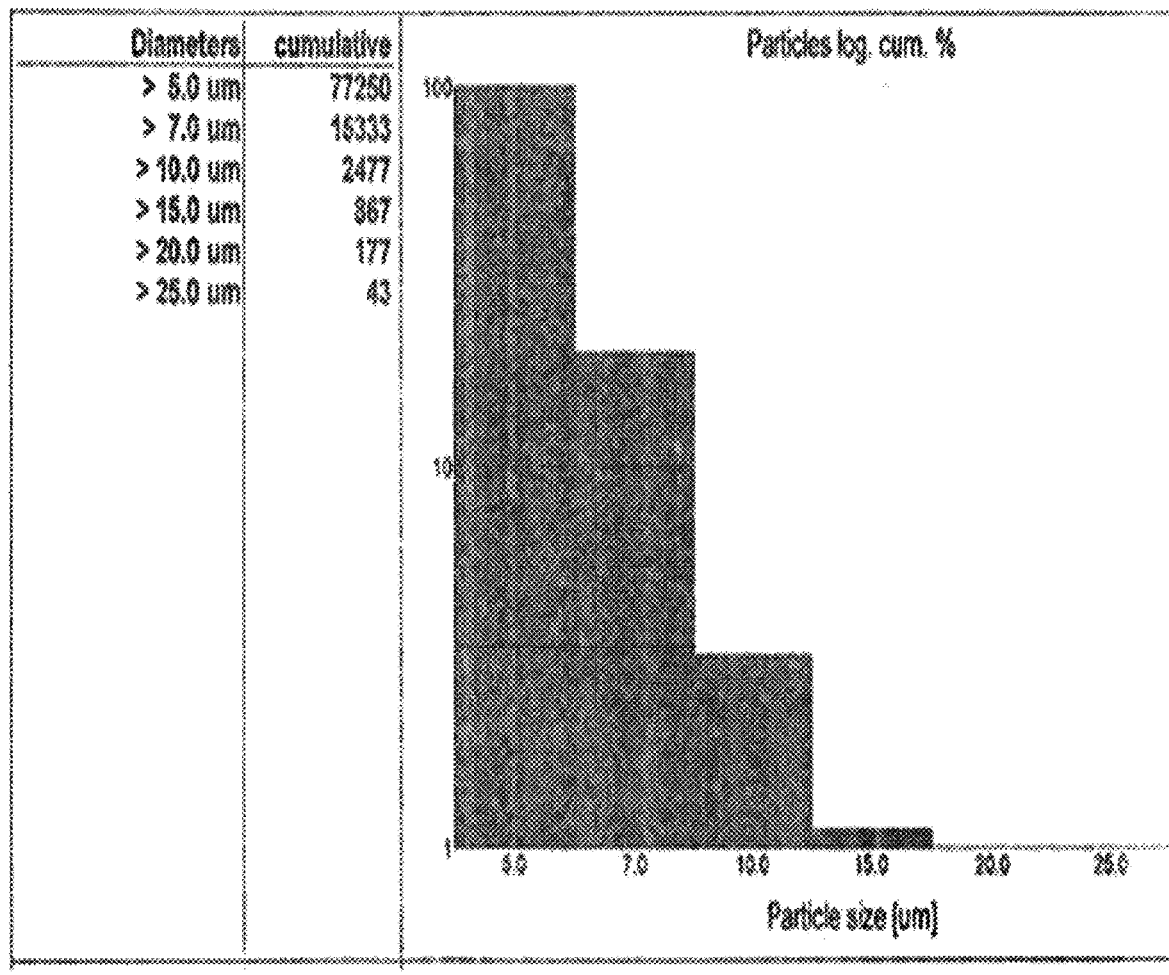
FIG. 2 is a graph illustrating the results of insoluble particle counts measured for a lyophilized cyclophosphamide composition (Comparison 1), in which t-butanol was used as a solvent instead of water for injection.

The thus-prepared lyophilized composition for injection of the present invention is comprised of insoluble particles, in which specifically, the cumulative number of particles having a diameter of 10 μm or greater is 6,000 or fewer per container and the number of particles having a diameter of 25 μm or greater is 600 or fewer per container, and thus it sufficiently meets the standard tolerance as an injection. In a specific embodiment of the present invention, it was confirmed that the number of insoluble particles was decreased in the lyophilized composition of the present invention, compared to the lyophilized compositions which were prepared using t-butanol (i.e., an organic solvent commonly used in the preparation of lyophilized cyclophosphamide compositions) as a solvent (FIGS. 1 and 2).

The lyophilized composition of the present invention may be provided by sealing in an amount corresponding to a determined volume of a container for injection, in which 50 mL to 500 mL of water for pharmaceutical use per 1,000 mg of anhydrous cyclophosphamide may be added, so that the composition can easily be used in the field, but the provision of the lyophilized composition is not limited thereto. For example, since the lyophilized composition of the present invention is provided by dispensing an amount of a single dose into containers capable of holding an adequate volume of a solution used for a single dose according to the U.S. Pharmacopeia (USP), the composition can be injected after preparing the same as a solution with a desired final concentration by injecting a solution (e.g., water for injection, etc.). For example, the lyophilized composition may be provided in an amount of 200 mg, 500 mg, 1 g, and 2 g by filling it into syringe containers capable of holding an amount of 10 mL, 25 mL, 50 mL, and 100 mL of a solution, respectively, based on the weight of anhydrous cyclophosphamide, so as to provide the same with the final concentration of 20 mg/mL, but the provision of the lyophilized composition is not limited thereto. Further, at the time of intravenous injection, the lyophilized composition can be administered at a concentration of at least 2 mg/mL, and thus, for example, anhydrous cyclophosphamide (1,000 mg) may be provided by filling it into containers into which 500 mL of water for pharmaceutical use can be injected, but the provision of the lyophilized composition is not limited thereto.

The lyophilized composition of the present invention, as described above, may be provided in the form of a cake having a porosity of 40% to 90%, but the provision of the lyophilized composition is not limited thereto.

Further, as described above, based on the increased solubility of the lyophilized composition prepared by the method of the present invention, the present invention provides a method for preparing a cyclophosphamide injection, which includes a first step of dissolving cyclophosphamide and a lyoprotectant in a water solvent in a reaction vessel at 40° C. to 70° C.; a second step of lyophilizing the solution obtained in the previous step to prepare a lyophilized cyclophosphamide composition; and a third step of adding 20 mL to 500 mL of water for pharmaceutical use to the lyophilized cyclophosphamide composition, which is obtained from the previous step, per 1 g of anhydrous cyclophosphamide. In particular, the step of dissolving the lyophilized cyclophosphamide composition by adding water for pharmaceutical use thereto can be achieved within 15 seconds, and the lyophilized cyclophosphamide composition used at this time may be in a state where 99% or more of the lyophilized cyclophosphamide composition is completely dissolved.

Considering the current cyclophosphamide injections used in clinical practice, a lyophilized composition containing cyclophosphamide in an amount of 1,000 mg based on the conventional anhydrous cyclophosphamide is dissolved in 50 mL of water for injection and administered at a concentration of 20 mg/mL. Alternatively, the lyophilized composition may be administered at a concentration of 2 mg/mL, which is an at least 10-fold diluted concentration thereof. Therefore, an injection using the lyophilized cyclophosphamide composition of the present invention may be prepared by adding 50 mL to 500 mL of water for injection to the lyophilized composition per 1 g of anhydrous cyclophosphamide. Alternatively, the lyophilized cyclophosphamide composition may be prepared as a stock solution at a higher concentration by adding an injection in a range of 20 mL to less than 50 mL thereto, and the stock solution can be diluted for use when administered. However, when the amount of the water for injection being added to dissolve the lyophilized composition corresponding to 1 g of anhydrous cyclophosphamide is less than 20 mL (e.g., 10 mL), the dissolution is incomplete, and thus, it is possible to visually confirm that the solution is opaque when observed against a black background with an illuminance of 1,000 lux. This could be also confirmed under a fluorescent lamp with an illuminance of about 300 lux or less.

DETAILED DESCRIPTION OF THE INVENTION

Hereinafter, the present invention will be described in more detail with reference to the following Examples. However, these Examples are intended to illustrate the present invention more specifically, and the scope of the invention is not limited by these Examples.

Example 1: Preparation of Solution of Raw Material Containing D-Mannitol as Lyoprotectant A sample, in which cyclophosphamide monohydrate (1.069 g) and D-mannitol (0.75 g) were mixed, was added to vials. Then, while adding water for injection (20 mL) to each vial having temperatures set at 20 □, 30 □, 35 □, 40 □, 45 □, 50 □, 55 □, 60 □, 70 □, and 80 □, the time was measured from the instant the water for injection was added to the instant the sample was completely dissolved in each. The mixture was maintained for up to a total of 30 minutes, filtered, and the content of cyclophosphamide present in the filtrate was measured. The measurement results are shown in Table 1 below.

TABLE 1

| Solubility Temperature (□) | Sample | Test 1 | Test 2 | Test 3 | Average Content (wt/wt %) |
|---|---|---|---|---|---|
| 20 | Sample 1 | Insoluble | Insoluble | Insoluble | 76.13 |
| 30 | Sample 2 | Partially soluble | Partially soluble | Partially soluble | 90.82 |
| 35 | Sample 3 | Partially soluble | Partially soluble | Partially soluble | 95.12 |
| 40 | Sample 4 | 8 min 50 sec | 8 min 36 sec | 8 min 58 sec | 100.29 |
| 45 | Sample 5 | 5 min 12 sec | 5 min 53 sec | 4 min 58 sec | 100.31 |
| 50 | Sample 6 | 3 min 10 sec | 2 min 58 sec | 3 min 05 sec | 100.43 |
| 55 | Sample 7 | 2 min 24 sec | 2 min 15 sec | 2 min 30 sec | 100.26 |
| 60 | Sample 8 | 1 min 25 sec | 1 min 42 sec | 1 min 10 sec | 100.29 |
| 70 | Sample 9 | 0 min 52 sec | 1 min 06 sec | 0 min 56 sec | 96.05 |
| 80 | Sample 10 | 0 min 37 sec | 0 min 30 sec | 0 min 32 sec | 76.48 |

The contents of Samples 1, 2, 4, 6, 8, 9, and 10 were calculated by the following equations, respectively.

| Sample | Equation | Content |
|---|---|---|
| Sample 10 | $\dfrac{0.5313 \times 25.3 \text{ mg}/50 \text{ mL} \times 1.00/1.00 \times 1.006 \times 100}{0.7071 \times 1000.2 \text{ mg}/20 \text{ mL} \times 2 \text{ mL}/20 \text{ mL} \times 2 \text{ mL}/20 \text{ mL}} =$ | 76.48 |
| Sample 9 | $\dfrac{0.6673 \times 25.3 \text{ mg}/50 \text{ mL} \times 1.00/1.00 \times 1.006 \times 100}{0.7071 \times 1000.3 \text{ mg}/20 \text{ mL} \times 2 \text{ mL}/20 \text{ mL} \times 2 \text{ mL}/20 \text{ mL}} =$ | 96.05 |
| Sample 8 | $\dfrac{0.6966 \times 25.3 \text{ mg}/50 \text{ mL} \times 1.00/1.00 \times 1.006 \times 100}{0.7071 \times 1000.1 \text{ mg}/20 \text{ mL} \times 2 \text{ mL}/20 \text{ mL} \times 2 \text{ mL}/20 \text{ mL}} =$ | 100.29 |
| Sample 6 | $\dfrac{0.6978 \times 25.3 \text{ mg}/50 \text{ mL} \times 1.00/1.00 \times 1.006 \times 100}{0.7071 \times 1000.4 \text{ mg}/20 \text{ mL} \times 2 \text{ mL}/20 \text{ mL} \times 2 \text{ mL}/20 \text{ mL}} =$ | 100.43 |
| Sample 4 | $\dfrac{0.6969 \times 25.3 \text{ mg}/50 \text{ mL} \times 1.00/1.00 \times 1.006 \times 100}{0.7071 \times 1000.5 \text{ mg}/20 \text{ mL} \times 2 \text{ mL}/20 \text{ mL} \times 2 \text{ mL}/20 \text{ mL}} =$ | 100.29 |
| Sample 2 | $\dfrac{0.6309 \times 25.3 \text{ mg}/50 \text{ mL} \times 1.00/1.00 \times 1.006 \times 100}{0.7071 \times 1000.2 \text{ mg}/20 \text{ mL} \times 2 \text{ mL}/20 \text{ mL} \times 2 \text{ mL}/20 \text{ mL}} =$ | 90.82 |
| Sample 1 | $\dfrac{0.5289 \times 25.3 \text{ mg}/50 \text{ mL} \times 1.00/1.00 \times 1.006 \times 100}{0.7071 \times 1000.3 \text{ mg}/20 \text{ mL} \times 2 \text{ mL}/20 \text{ mL} \times 2 \text{ mL}/20 \text{ mL}} =$ | 76.13 |

Additionally, in order to confirm the critical temperature showing a rapid change in content, the temperature range of 70° C. to 80° C., at which the content is rapidly reduced, was subdivided, and then the experiment was performed in the same manner as above using water for injection having a temperature of 72° C., 75° C., and 78° C. The results are shown in Table 2 below.

TABLE 2

| Solubility Temperature (° C.) | Sample | Test 1 | Test 2 | Test 3 | Average Content (wt/wt %) |
|---|---|---|---|---|---|
| 78 | Sample 11 | 0 min 38 sec | 0 min 39 sec | 0 min 42 sec | 78.63 |
| 75 | Sample 12 | 0 min 45 sec | 0 min 53 sec | 0 min 45 sec | 89.39 |
| 72 | Sample 13 | 0 min 49 sec | 0 min 49 sec | 0 min 49 sec | 93.94 |

The contents of Samples 11 to 13 were calculated by the following equations, respectively.

| Sample | Equation | Content |
|---|---|---|
| Sample 11 | $\dfrac{0.5670 \times 25.5 \text{ mg}/50 \text{ mL} \times 261.09/279.10 \times 1.006 \times 100}{0.6922 \times 1000.0 \text{ mg}/1000 \text{ mL} \times 25 \text{ mL}/50 \text{ mL}} =$ | 78.63 |
| Sample 12 | $\dfrac{0.6446 \times 25.5 \text{ mg}/50 \text{ mL} \times 261.09/279.10 \times 1.006 \times 100}{0.6922 \times 1000.0 \text{ mg}/1000 \text{ mL} \times 25 \text{ mL}/50 \text{ mL}} =$ | 89.39 |
| Sample 13 | $\dfrac{0.6774 \times 25.5 \text{ mg}/50 \text{ mL} \times 261.09/279.10 \times 1.006 \times 100}{0.6922 \times 1000.0 \text{ mg}/1000 \text{ mL} \times 25 \text{ mL}/50 \text{ mL}} =$ | 93.94 |

Example 2: Sterility Test after Sterile Filtration and Test of Changes in Content Similarly to Example 1, after sterilizing the solutions prepared at various temperatures using a membrane filter having a pore size of 0.2 μm, the changes in the solutions were confirmed by performing the sterility test and by measuring the cyclophosphamide content. As a result, the solutions were determined to be suitable in the sterility test after the membrane filtration at all temperature conditions, and additionally, there were almost no changes in the content of cyclophosphamide according to the sterilization process by membrane filtration.

Example 3: Mass Production of Lyophilized Composition for Injection Containing D-Mannitol as Lyoprotectant (Sample 14)

Vials and raw materials in an amount for 1,000 vial contents were prepared as shown in Table 3 below.

TABLE 3

| Raw Material | Amount of Active Ingredient | Standard | Dose (per vial) | Amount Used (g) |
|---|---|---|---|---|
| Cyclophosphamide Hydrate | Anhydrous | USP | 1 g | 1,069 g (monohydrate) |
| D-Mannitol | | KP | 750 mg | 750 g |
| Water for Injection | | USP | 20 mL | 20 L |
| Vial (50 cm³, colorless) | | KP | 1 | 1,000 |
| Vial Cap | | — | 1 | 1,000 |
| Lyophilization Rubber Stopper | | KP | 1 | 1,000 |

TABLE 4

| | Freezing | Decompression | 1 | 2 | 3 | 4 | 5 | 6 | 7 | 8 | Total Time minutes | hours |
|---|---|---|---|---|---|---|---|---|---|---|---|---|
| Rack Temp. (° C.) | −40 | | −15 | −15 | 0 | 0 | 0 | 0 | 0 | 0 | | |
| Time (minutes) | 300 | | 120 | 1,500 | 240 | 600 | 120 | 480 | 120 | 1,200 | 4,380 | 73 |
| Vacuum (mTorr) | — | 250 | 250 | 250 | 250 | 250 | 500 | 700 | 700 | 700 | | |

Condenser set temperature: −40□

As shown above, 1,000 vials of cyclophosphamide hydrate and D-mannitol were prepared by dissolving them in water for injection. Specifically, the raw materials in the amounts shown above were added into a reaction vessel along with water for injection (20 L) and dissolved while maintaining the reaction vessel at 40° C. to 70° C. Specifically, the oxygen content was reduced by replacing it with nitrogen for 10 minutes. Then, the raw materials in the amounts shown in Table 1 above and the water for injection heated to 50° C. (about 18 L) were added into a preparation tank. The mixture was completely dissolved by stirring, and water for injection was further added thereto to a final volume of 20 L. The stirring of the solution was stopped upon confirmation of complete dissolution of the raw materials.

The solution was filtered by applying a nitrogen pressure in the preparation tank containing the raw material solution (20 L) prepared as described above. A filter integrity test was performed using a Sartocheck4 integrity tester before and after the filtration, and the suitability of the filter was determined by measuring the values of bubble points. When the filtration was completed, the raw material solution was transferred to a filling process.

Vial caps and filling components were washed using purified water and water for injection, and they were sterilized in a high-pressure steam sterilizer. The lyophilization rubber stopper was sterilized in an autoclave without washing it with a dust-free rubber stopper. The vials were sterilized using a tunnel sterilizer after washing with an automatic vial washer. The solution (20 L) transferred to the filling process was dispensed in equal amounts into each of the 1,000 vials sterilized and prepared above. Specifically, the solution was filled while adjusting the filling rate by arranging vials using a large-scale vial-filling machine. The solution was filled in an amount of 20 mL per vial, and rubber stoppers were half-capped for lyophilization. Once the filling was completed, the resultants were transferred to a lyophilization process.

The filled vials which were transferred to the lyophilization process were arranged in trays and carefully inserted into the chamber of a lyophilizer in sequential order from the top rack to the bottom rack. After inserting all of the trays into the chamber, three temperature sensors in the chamber were placed within the vials in each rack. After confirming the tray alignment again, the gate of the lyophilizer was completely sealed. Then, the vials were lyophilized according to the conditions shown in Table 4 below.

After releasing the vacuum by replacing it with nitrogen, the lyophilization rubber stoppers were tightly capped in a vacuum state using an automatic stopper device. The vials were sealed by adjusting the automatic sealing machine to the height of the vials. Vials for which sealing conditions were poor or rubber stoppers were damaged were discarded. The products for which the lyophilization is completed as such were then transferred to a foreign material inspection process. Specifically, the impurities inspection of the transferred products was performed by the naked eye against black and white backgrounds under the illumination of 1,000 lux or more directly under a white light source.

Example 4: Dose of D-Mannitol and Changes in Dissolution Time According to Vial Filling Conditions Lyophilized compositions were prepared in vials for injection with the contents shown in Table 5 below, respectively. While adding water for injection (50 mL) into each vial, the dissolution time until complete dissolution of each of the lyophilized compositions was measured. The results are shown in Table 6. Additionally, lyophilized compositions were prepared using D-mannitol in an amount of 0.75 g, 2 g, and 0.1 g per vial, and these lyophilized compositions were named as Samples 14 to 16, respectively.

TABLE 5

| | Amount of Raw Materials (g) | | |
|---|---|---|---|
| | Cyclophosphamide Hydrate | D-Mannitol | Water for Injection (mL) |
| Sample 14 | 1.069 | 0.75 | 20 |
| Sample 15 | 1.069 | 2 | 20 |
| Sample 16 | 1.069 | 0.1 | 20 |

TABLE 6

| | Dissolution Time (Dissolution Time after Injection of Water for Injection) | | |
|---|---|---|---|
| | Test 1 | Test 2 | Test 3 |
| Sample 14 | 5 sec | 8 sec | 7 sec |
| Sample 15 | 10 sec | 9 sec | 12 sec |
| Sample 16 | 12 sec | 10 sec | 14 sec |

As shown in Table 6, when lyophilized compositions were prepared using D-mannitol in an amount of 0.1 g to 2 g, the time required for complete dissolution of the entire lyophilized composition, when water for injection was added thereto, was as fast as within 15 seconds for all of the lyophilized compositions. This result suggests that the use of D-mannitol (i.e., a lyoprotectant) within the range described above is advantageous for cake formation, and eventually, when lyophilized compositions are dissolved by the addition of water for injection, it facilitates water permeation, thus showing the effect described above.

Example 5: Measurement of Insoluble Particles

Insoluble particles existing among the prepared lyophilized composition were counted. The particles satisfied the standard tolerance, in which 6,000 or fewer particles per container should have a diameter of 10 μm or greater, while 600 or fewer particles per container should have a diameter of 25 μm or greater. The measurement results are shown in FIG. 1. Meanwhile, the measurement results of the lyophilized composition in Comparison 1 prepared using t-butanol instead of water for injection are shown in FIG. 2.

As shown in FIGS. 1 and 2, it was confirmed that the cumulative number of the insoluble particles having a size of 10 μm or greater was 1,640 per container in Sample 11 of the present invention, whereas Comparison 1, in which insoluble particles were prepared using t-butanol (i.e., an organic solvent), contained 2,477 insoluble particles, which was much greater than the cumulative number of those in Sample 11.

Example 6: Measurement of Porosity

The pore size of Samples 14 and 15 (including 0.75 g and 2.0 g of D-mannitol, respectively) and the cyclophosphamide powder (i.e., a raw material) in Comparison 2 of the present invention was measured. The porosity measurement was performed by the Korea Polymer Testing & Research Institute (KOPTRI), an accredited international testing agency, by requesting the samples prepared by the present applicant. The measurement results for Samples 14 and 15 and Comparison 2 are shown in Table 7 below.

TABLE 7

| Sample | Items for Analysis | Unit | Result |
|---|---|---|---|
| Sample 14 | Apparent density | g/cm$^3$ | 0.59 |
| | Average diameter | μm | 0.43 |
| | Porosity | % | 57.8 |
| Sample 15 | Apparent density | g/cm$^3$ | 0.32 |
| | Average diameter | μm | 14.8 |
| | Porosity | % | 80.9 |
| Comparison 2 | Apparent density | g/cm$^3$ | 1.31 |
| | Average diameter | μm | 0.02 |
| | Porosity | % | 5.24 |

As shown in Table 7 above, it was confirmed that the cyclophosphamide powder (i.e., a raw material) has a very low porosity and consequently a significantly high density because the cyclophosphamide powder does not contain D-mannitol, which is a lyoprotectant. These results indicate that the formulation is not suitable for use in the field because the formulation is compactly condensed with raw materials and thus cannot easily be dissolved by water for injection.

Figure 3:
FIG. 3 is an image illustrating a lyophilized cyclophosphamide composition in a cake form formed by lyophilization in a vial for injection using D-mannitol as a lyoprotectant.
Figure 4:
FIG. 4 is an image illustrating a lyophilized cyclophosphamide composition in a cake form formed by lyophilization in a vial for injection using lactose as a lyoprotectant.

Examples 7 and 8: Preparation of Lyophilized Composition for Injection Containing D-Mannitol or Lactose as Lyoprotectant Vials for injection, which contain a lyophilized cyclophosphamide composition, were prepared according to Example 3 using D-mannitol and in a manner similar to Example 3 except that lactose was used instead of D-mannitol. Specifically, cyclophosphamide hydrate (2.67 g) was added into a 50 mL flask and dissolved by adding water for injection (about 25 mL) at 55 □ thereinto. D-Mannitol (1.87 g) and lactose (1.87 g) were dissolved by adding them into the cyclophosphamide solution, and the resulting mixed solution was filled with water for injection up to 50 mL. The mixed solution was dispensed into 50 cc vials in an amount of 10 mL each, lyophilized and sealed in the same manner as in Example 3, and thereby the vials for injection containing a lyophilized cyclophosphamide composition were prepared. Cake formation was visually confirmed and photographed, and the results are shown in FIGS. 3 and 4. As shown in FIGS. 3 and 4, when the lyophilized composition was prepared using D-mannitol and lactose as a lyoprotectant, good quality cakes were uniformly formed.

Figure 5:
FIG. 5 is an image illustrating a lyophilized cyclophosphamide composition in a cake form prepared using sorbitol as a lyoprotectant instead of D-mannitol or lactose.
Figure 6:
FIG. 6 is an image illustrating a lyophilized cyclophosphamide composition in a cake form prepared sucrose as a lyoprotectant instead of D-mannitol or lactose.
Figure 7:
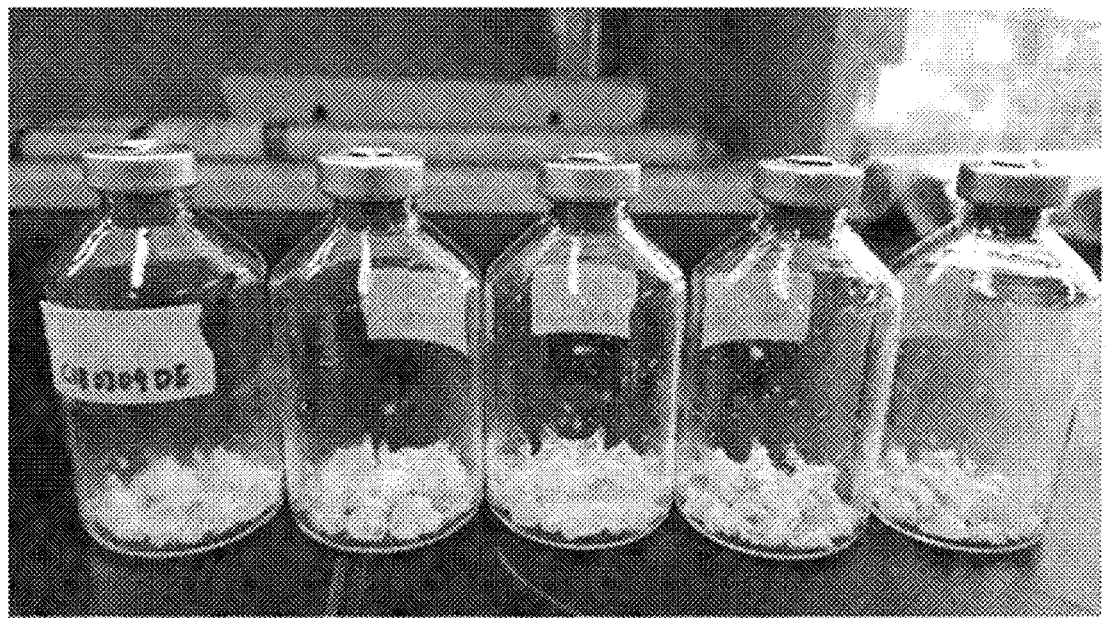
FIG. 7 is an image illustrating a lyophilized cyclophosphamide composition in a cake form prepared using dextrose as a lyoprotectant instead of D-mannitol or lactose.
Figure 8:
FIG. 8 is an image illustrating the solubility of lyophilized cyclophosphamide compositions in water for injection, in which the lyophilized cyclophosphamide compositions were prepared using sorbitol, sucrose, dextrose, and lactose (from left to right) as a lyoprotectant, respectively.

Comparative Examples 1 to 3: Preparation of Lyophilized Composition for Injection Containing Sorbitol, Sucrose, or Dextrose as Lyoprotectant Vials for injection containing a lyophilized cyclophosphamide composition were prepared in the same manner as in Examples 7 and 8 except that sorbitol, sucrose, or dextrose was used in an equal amount instead of D-mannitol or lactose. Further, cake formation in these compositions was visually confirmed and photographed, and the results are shown in FIGS. 5 to 7, respectively. As shown in FIGS. 5 to 7, uniformly formed cakes were not observed in these lyophilized compositions, and they existed as irregular masses. Further, in order to confirm the solubility of these lyophilized compositions, 500 mg of anhydrous cyclophosphamide contained in each vial was dissolved by injecting 25 mL of water for injection into each vial, and the results were photographed and are shown in FIG. 8 (from left to right: sorbitol, sucrose, and dextrose). For comparison, the lyophilized composition prepared using lactose as a lyoprotectant was dissolved under the same conditions and photographed, and the result is shown together in FIG. 8 (rightmost). As shown in FIG. 8, it was confirmed that the lyophilized composition prepared using lactose was completely dissolved within a short period of time, whereas all of the lyophilized compositions prepared using sorbitol, sucrose, and dextrose were not completely dissolved, and a significant amount of these remained in a solid state.

Example 9: Long-Term Storage Stability

In order to confirm the long-term storage stability of the lyophilized cyclophosphamide compositions prepared in vials for injection according to the present invention, a stability test was performed according to the U.S. Pharmacopoeia (USP) standard while storing the lyophilized cyclophosphamide compositions at 25±2° C. and a relative humidity of 60±5% for 9 months from the date of preparation. Specifically, five test items (i.e., i) appearance; ii) transparency, completeness, and dissolution state by detection of the presence of insoluble impurities; iii) confirmation of ingredients by TLC and HPLC; iv) pH; and v) quantitative method) and additionally moisture content were tested at 3-month intervals. Each test standard is shown in Table 8 below. Based on Table 8, products prepared at different times and in different batches were repeatedly tested. As a result, it was confirmed that the products had suitable specifications in all of the test items, and they were maintained even after time passed. The test results are shown in Table 9 below. In addition, as shown in Table 9, the moisture content was maintained at a low level to be within 1±0.1%.

TABLE 8

| Test Items | Standard |
|---|---|
| Appearance | Colorless transparent vial containing white lyophilized powder |
| Dissolution State | Rf and color are the same as those of standard solution on TLC phase |
| | Main peak retention time is the same as that of standard solution on HPLC phase |
| Confirmation of Ingredients | Transparency is similar to that of Comparative solution and Complete dissolution |
| | No detection of insoluble impurities |
| pH | pH 3.0 to 9.0 |
| Quantitative Method | 90.0☐ to 110☐ based on anhydrous cyclophosphamide 500 mg/vial |
| Moisture Content | Reference value |

TABLE 9

| | | Test Period (Duration/Month) | | | |
|---|---|---|---|---|---|
| Test Items | Standard | Initial | 3 Months | 6 Months | 9 Months |
| Appearance | Colorless transparent vial containing white lyophilized powder | colorless transparent vial containing white lyophilized powder | colorless transparent vial containing white lyophilized powder | colorless transparent vial containing white lyophilized powder | colorless transparent vial containing white lyophilized powder |
| Dissolution State | Transparency and Completeness | conform to standard | conform to standard | conform to standard | conform to standard |
| | Insoluble impurities | not detected | not detected | not detected | not detected |
| Confirmation Test | TLC | conform to standard | conform to standard | conform to standard | conform to standard |
| | HPLC | conform to standard | conform to standard | conform to standard | conform to standard |
| pH | 3.0 to 9.0 | 5.1 | 5.0 | 4.9 | 4.9 |
| Quantitative Method | Anhydrous cyclophosphamide 500 mg/vial 90.0% to 110.0% | 101.3% | 100.8% | 100.5% | 100.4% |
| Moisture Content | Reference value | 0.9% | 1.1% | 1.0% | 1.1% |
| | Decision | appropriate | appropriate | appropriate | appropriate |
| | Test Date | Apr. 17, 2017 | Jul. 19, 2017 | Oct. 17, 2017 | Jan. 17, 2018 |

Further, in order to confirm the long-term storage stability, the above test was further performed by extending the storage period up to 18 months. The same experiment was performed on two different samples at different time periods, and the results are shown in Tables 10 and 11, respectively. As shown in Tables 10 and 11, it was confirmed that even when the storage period was extended up to 18 months, the lyophilized cyclophosphamide compositions had suitable specifications in all of the test items, and they were maintained even after time passed.

The invention claimed is:

1. A method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, comprising:
   a first step of dissolving D-mannitol or lactose, as a lyoprotectant, and cyclophosphamide in a water solvent in a reaction vessel at 40° C. to 70° C.;

TABLE 10

| Test Items | Standard | | Test Period (Duration/Month) | | | | | |
| --- | --- | --- | --- | --- | --- | --- | --- | --- |
| | | | Initial | 3 Months | 6 Months | 9 Months | 12 Months | 18 Months |
| Appearance | Colorless transparent vial containing white lyophilized powder | | colorless transparent vial containing white lyophilized powder | colorless transparent vial containing white lyophilized powder | colorless transparent vial containing white lyophilized powder | colorless transparent vial containing white lyophilized powder | colorless transparent vial containing white lyophilized powder | colorless transparent vial containing white lyophilized powder |
| Dissolution State | | Transparency and Completeness | conform to standard | conform to standard | conform to standard | conform to standard | conform to standard | conform to standard |
| | | Insoluble impurities | not detected | not detected | not detected | not detected | not detected | not detected |
| Confirmation Test | | TLC | conform to standard | conform to standard | conform to standard | conform to standard | conform to standard | conform to standard |
| | | HPLC | conform to standard | conform to standard | conform to standard | conform to standard | conform to standard | conform to standard |
| pH | 3.0 to 9.0 | | 5.1 | 5.0 | 4.9 | 4.9 | 5.0 | 5.1 |
| Quantitative Method | Anhydrous cyclophosphamide 500 mg/vial 90.0% to 110.0% | | 101.3% | 100.8% | 100.5% | 100.4% | 100.5% | 100.4% |
| Decision | | | appropriate | appropriate | appropriate | appropriate | appropriate | appropriate |
| Test Date | | | Apr. 17, 2017 | Jul. 19, 2017 | Oct. 17, 2017 | Jan. 17, 2018 | Apr. 17, 2018 | Oct. 17, 2018 |

TABLE 11

| Test Items | Standard | | Test Period (Duration/Month) | | | | | |
| --- | --- | --- | --- | --- | --- | --- | --- | --- |
| | | | Initial | 3 Months | 6 Months | 9 Months | 12 Months | 18 Months |
| Appearance | colorless transparent vial containing white lyophilized powder | | colorless transparent vial containing white lyophilized powder | colorless transparent vial containing white lyophilized powder | colorless transparent vial containing white lyophilized powder | colorless transparent vial containing white lyophilized powder | colorless transparent vial containing white lyophilized powder | colorless transparent vial containing white lyophilized powder |
| Dissolution State | | Transparency and Completeness | conform to standard | conform to standard | conform to standard | conform to standard | conform to standard | conform to standard |
| | | Insoluble impurities | not detected | not detected | not detected | not detected | not detected | not detected |
| Confirmation Test | | TLC | conform to standard | conform to standard | conform to standard | conform to standard | conform to standard | conform to standard |
| | | HPLC | conform to standard | conform to standard | conform to standard | conform to standard | conform to standard | conform to standard |
| pH | 3.0 to 9.0 | | 5.3 | 5.3 | 5.3 | 5.2 | 5.3 | 5.2 |
| Quantitative Method | Anhydrous cyclophosphamide 500 mg/vial 90.0% to 110.0% | | 100.6% | 100.1% | 100.3% | 100.0% | 100.1% | 100.2% |
| Decision | | | appropriate | appropriate | appropriate | appropriate | appropriate | appropriate |
| Test Date | | | Jun. 20, 2017 | Sep. 20, 2017 | Dec. 20, 2017 | Mar. 20, 2018 | Jun. 20, 2018 | Dec. 20, 2018 | a second step of filling the solution obtained in the previous step into a vial prepared by sterilization; and a third step of lyophilizing the cyclophosphamide solution filled into the vial.

2. The method of claim 1, wherein the water for pharmaceutical use is water for injection, drinking water, purified water, sterile purified water, sterile water for injection, bacteriostatic water for injection, distilled water, or normal saline.

3. The method of claim 1, wherein in the first step, the cyclophosphamide is used in an amount of 0.01 g to 0.1 g per 1 mL of a water solvent based on anhydrous cyclophosphamide.

4. The method of claim 1, wherein the lyoprotectant is used in an amount of 5 to 250 parts by weight based on 100 parts by weight of anhydrous cyclophosphamide.

5. The method of claim 1, wherein the cyclophosphamide is used in a concentration of 0.01 g/mL to 0.1 g/mL based on anhydrous cyclophosphamide, and the lyoprotectant is used in an amount of 5 to 250 parts by weight based on 100 parts by weight of anhydrous cyclophosphamide.

6. The method of claim 1, further comprising a step of sterilizing the solution between the first step and the second step.

7. The method of claim 1, wherein the third step is performed by cooling and maintaining the temperature at −40° C. or below while maintaining a vacuum of 200 mTorr to 1000 mTorr.

8. The method of claim 1, further comprising a step of sealing after the third step.

9. The method of claim 1, wherein a lyophilized composition in the form of a cake having a porosity of 40% to 90% is provided.

10. A method for preparing a lyophilized cyclophosphamide composition, wherein 99% or more of the finally prepared lyophilized cyclophosphamide composition is reconstituted within 15 seconds when water for pharmaceutical use is injected thereinto at a ratio of 50 mL per 1 g of anhydrous cyclophosphamide, comprising:

a first step of dissolving 0.01 g to 0.1 g of cyclophosphamide per 1 mL of a water solvent based on weight of the anhydrous cyclophosphamide; and 5 to 250 parts by weight of D-mannitol or lactose based on 100 parts by weight of the anhydrous cyclophosphamide in the water for pharmaceutical use in a reaction vessel at 40° C. to 70° C.;

a second step of sterilizing the solution obtained in the previous step by filtration with a membrane having a size of 0.2 μm or less and dispensing the solution into a container for injection;

a third step of lyophilizing the solution dispensed into the container to form a lyophilized cake; and a fourth step of sealing.

11. A lyophilized composition for injection prepared by the method of claim 1.

12. The lyophilized composition of claim 11, wherein the lyophilized composition 6 to 8 parts by weight of water and 5 to 250 parts by weight of D-mannitol or lactose based on 100 parts by weight of anhydrous cyclophosphamide, wherein 99% or more of the lyophilized composition for injection is reconstituted within 15 seconds when water for pharmaceutical use is injected thereinto at a ratio of 50 ml per 1 g of the anhydrous cyclophosphamide.

13. A lyophilized composition for injection prepared by the method of claim 10.

14. The lyophilized composition of claim 11, wherein the lyophilized composition is provided being sealed in a container for injection with a predetermined volume, which allows 50 mL to 500 ml of water for pharmaceutical use to be added per 1,000 mg of anhydrous cyclophosphamide, in an amount corresponding thereto.

15. A method for preparing a cyclophosphamide injection, comprising:

a first step of dissolving cyclophosphamide; and D-mannitol or lactose in a water solvent in a reaction vessel at 40° C. to 70° C.;

a second step of lyophilizing the solution obtained in the previous step to prepare a lyophilized cyclophosphamide composition; and a third step of adding 20 mL to 500 ml of water for pharmaceutical use to the lyophilized cyclophosphamide composition per 1 g of anhydrous cyclophosphamide.

16. The method of claim 15, wherein the third step is achieved within 15 seconds.

17. The lyophilized composition of claim 13, wherein the lyophilized composition comprises 6 to 8 parts by weight of water and 5 to 250 parts by weight of D-mannitol or lactose based on 100 parts by weight of anhydrous cyclophosphamide, wherein 99% or more of the lyophilized composition for injection is reconstituted within 15 seconds when water for pharmaceutical use is injected thereinto at a ratio of 50 ml per 1 g of the anhydrous cyclophosphamide.

18. The lyophilized composition of claim 13, wherein the lyophilized composition is provided being sealed in a container for injection with a predetermined volume, which allows 50 mL to 500 ml of water for pharmaceutical use to be added per 1,000 mg of anhydrous cyclophosphamide, in an amount corresponding thereto.

* * * * *